United States Patent [19]

Becht

[11] 4,442,964

[45] Apr. 17, 1984

[54] PRESSURE SENSITIVE AND WORKING-GAP CONTROLLED SURGICAL STAPLING INSTRUMENT

[75] Inventor: Carl T. Becht, Cincinnati, Ohio

[73] Assignee: Senco Products, Inc., Cincinnati, Ohio

[21] Appl. No.: 327,932

[22] Filed: Dec. 7, 1981

[51] Int. Cl.³ ............................................. A61B 17/04
[52] U.S. Cl. .................................. 227/8; 128/334 R; 227/19; 227/155
[58] Field of Search ............. 128/334 R; 227/DIG. 1, 227/19, 155, 8

[56] References Cited

U.S. PATENT DOCUMENTS

| | | | |
|---|---|---|---|
| 3,494,533 | 2/1970 | Green et al. | 227/DIG. 1 |
| 4,296,881 | 10/1981 | Lee | 227/30 X |
| 4,305,539 | 12/1981 | Korolkov et al. | 227/19 X |
| 4,315,589 | 2/1982 | Soong | 227/155 |
| 4,354,628 | 10/1982 | Green | 227/19 |

FOREIGN PATENT DOCUMENTS 1339394 12/1973 United Kingdom .................. 227/19

*Primary Examiner*—Paul A. Bell
*Attorney, Agent, or Firm*—Frost & Jacobs

[57] ABSTRACT

A surgical stapling instrument for suturing tissues or organs. The instrument is of the type having a fixed anvil jaw, a movable staple cartridge-carrying jaw shiftable toward and away from the anvil jaw, and a staple driver actuator shiftable to actuate the staple driver of the staple cartridge to implant the staples of the cartridge in the tissue or organ located between the anvil jaw and the staple cartridge-carrying jaw. The instrument is provided with a clutch to control the gap between the fixed anvil jaw and the staple cartridge in response to the pressure being applied to the organ or tissue therebetween to preclude over-compression or under-compression thereof. The instrument is also provided with a latch to preclude shifting of the staple driver actuator to actuate the staple driver when the gap determined by the clutch is not within the limits of the proper working gap of the instrument required by the forming limits of the staples. The latch means further assures proper sequential operation of the instrument by the surgeon.

25 Claims, 25 Drawing Figures

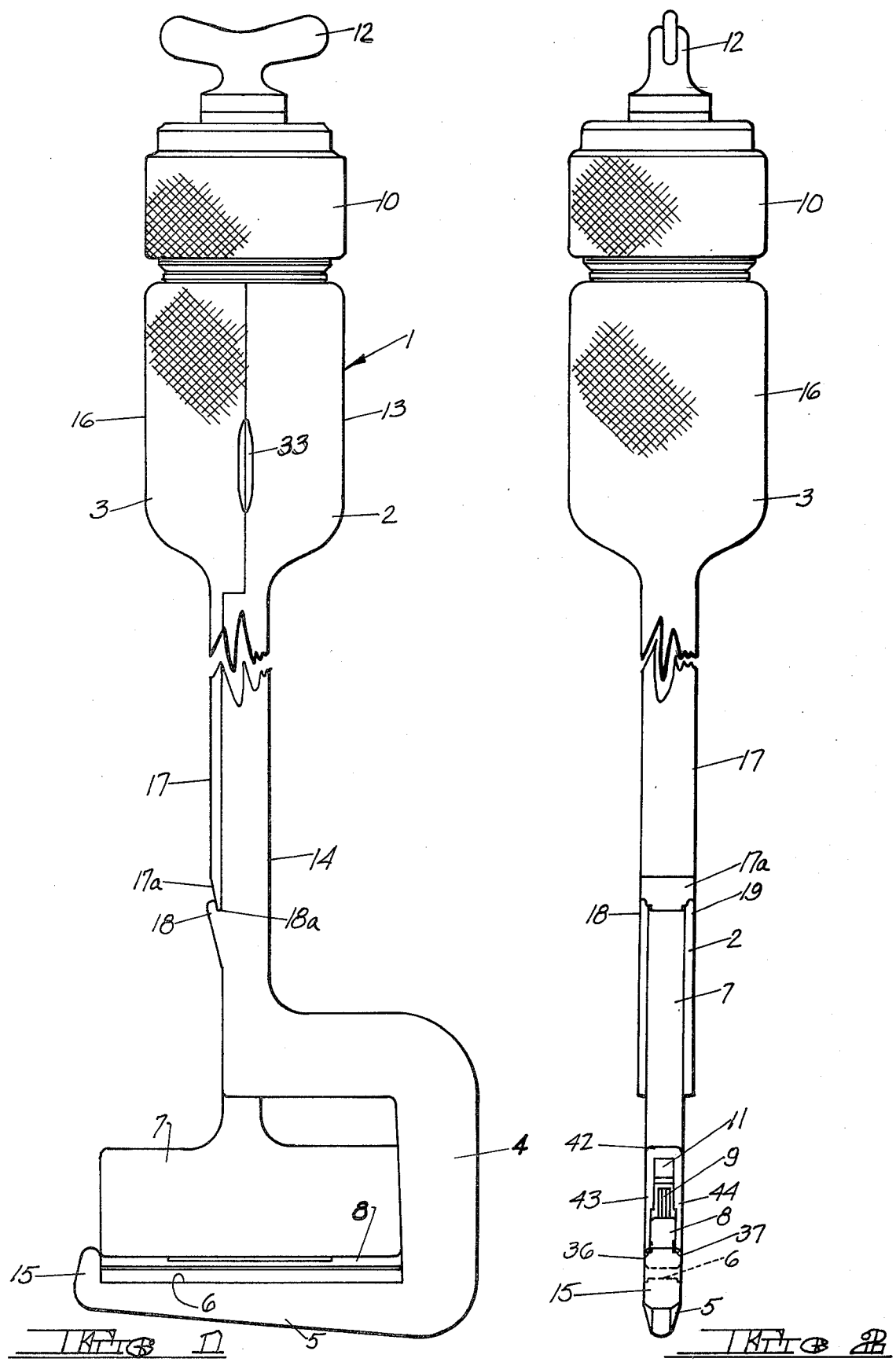

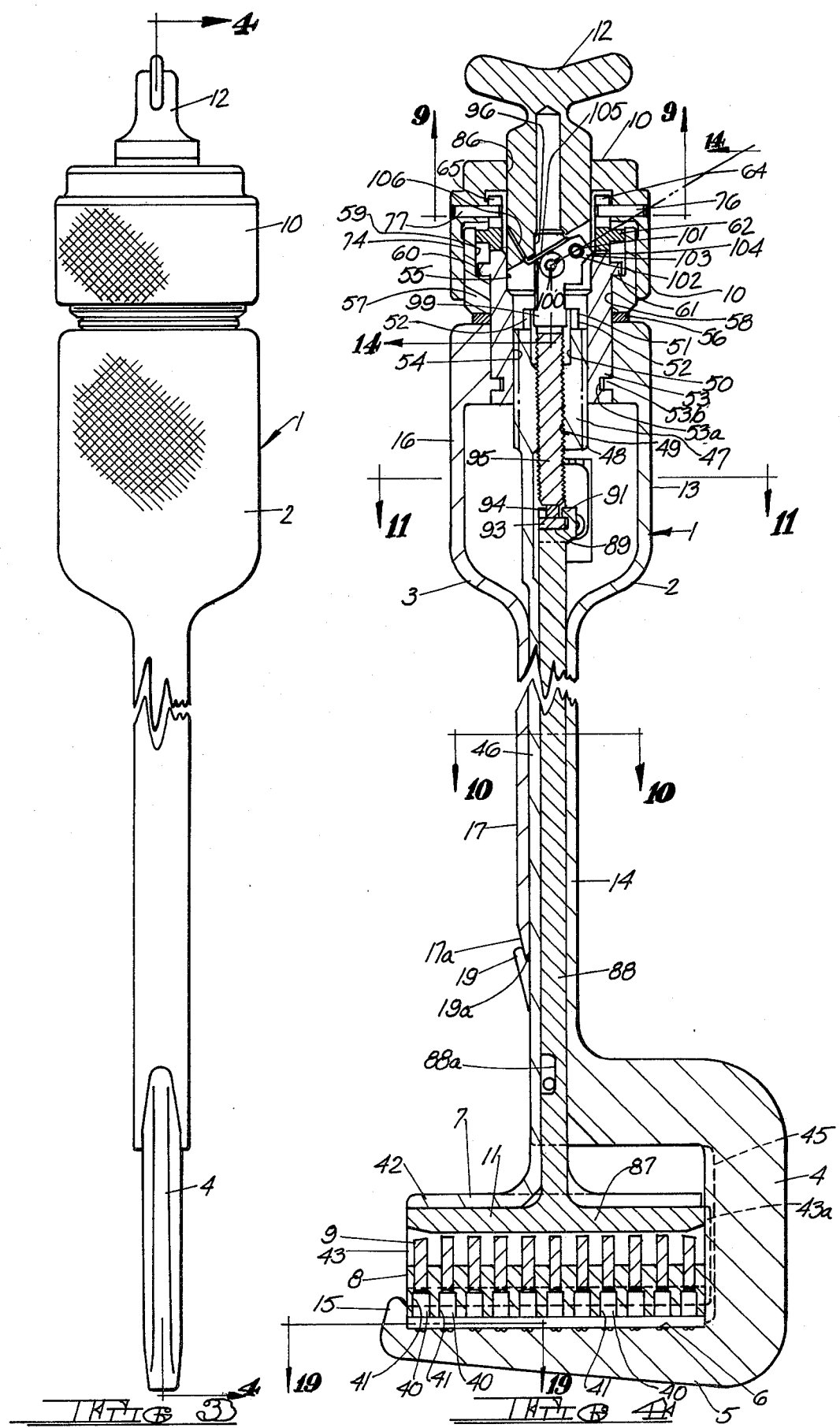

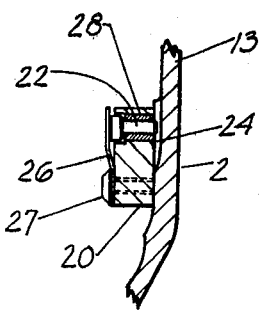
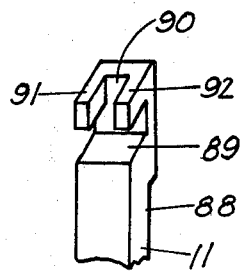
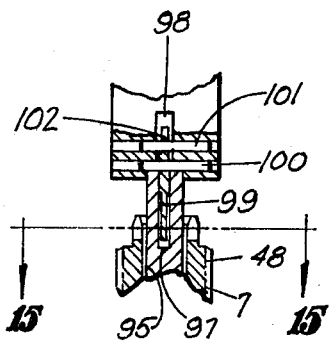
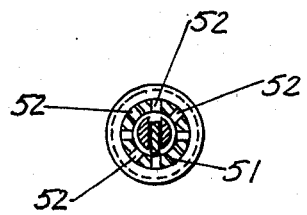
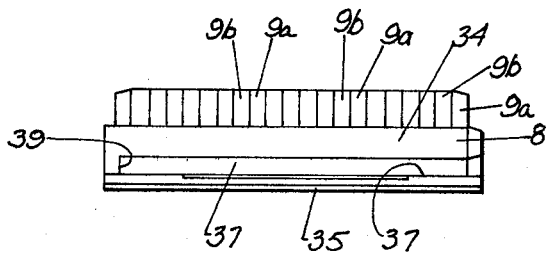
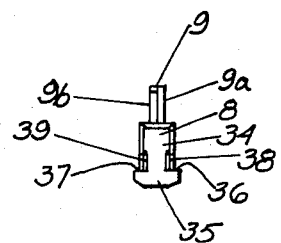
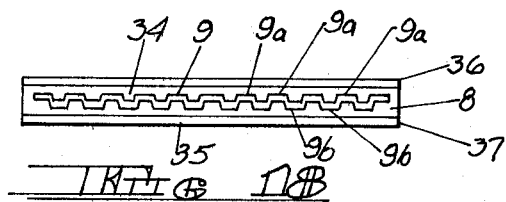

PRESSURE SENSITIVE AND WORKING-GAP CONTROLLED SURGICAL STAPLING INSTRUMENT

BACKGROUND OF THE INVENTION

The invention relates to a surgical stapling instrument for suturing tissue or organs and more particularly to such an instrument which is sensitive to the pressure being applied to the tissue or organ by the instrument and which is working gap-controlled.

Prior art workers have devised numerous embodiments of the type of surgical stapling instrument to which the improvements of the present invention are directed. Examples of such surgical stapling instruments are taught in U.S. Letters Pat. Nos. 3,080,564; 3,252,643; 3,269,630; 3,275,211; 3,315,863; 3,494,533; 3,589,589 and 3,795,034. All such surgical stapling instruments are intended for use in suturing tissue or organs such as pulmonary tissue, gastric stumps, bronchial stumps, small and large intestines, the stomach, the duodenum and the like. These prior art surgical stapling instruments are, in general, characterized by a fixed anvil or anvil supporting jaw and a movable staple cartridge-carrying jaw. The staple cartridge-carrying jaw is shiftable toward and away from the anvil jaw. The organ or tissue to be sutured is located between the fixed anvil jaw and the shiftable staple cartridge-carrying jaw.

The typical staple cartridge contains staples arranged to provide one or more staple suture lines. The cartridge is also provided with one or more staple drivers which, when shifted toward the fixed jaw of the instrument, will cause the staples to be driven from the cartridge and through the tissue or organ. The staples will be clinched by staple clinching grooves in the anvil portion of the fixed jaw. Finally, each such instrument is typically provided with a staple driver actuator by which the surgeon may cause the staple sutures to be implanted and clinched.

Prior art workers have devised various means to shift the staple cartridge-carrying jaw toward the fixed jaw. The most commonly encountered means is a hand-operated screw mechanism which directly powers the staple cartridge-carrying jaw toward the fixed anvil jaw. It will be understood that, for proper operation of the surgical instrument, the working gap between the staple cartridge-carrying jaw and the anvil jaw, in which the organ or tissue to be sutured is located, should be within the forming limits of the staples. In other words, the staples must be adequately clinched while, on the other hand, they must not be deformed or crushed.

With prior art surgical stapling instruments of the type under consideration, the surgeon simply rotated the screw mechanism (or manipulated some other form of advancing means) to shift the staple cartridge-carrying jaw toward the fixed anvil jaw until a predetermined gap or distance between the jaws, within the working gap of the instrument and its staples, was attained. The difficulty with this arrangement lies in the fact that the thickness and compressibility of organs and tissues vary. Therefore, when the staple cartridge-carrying jaw is driven or shifted to a predetermined distance from the fixed anvil jaw, it is very improbable that a correct compression will be placed on the organ or tissue to be sutured. If the organ or tissue is over-compressed, it can become strangulated and can undergo necroses. On the other hand, if the tissue or organ is under-compressed, hemostasis of the suture line will not be achieved with the accompanying well known undesirable effects.

The surgical instrument of the present invention overcomes this difficulty by driving the staple cartridge-carrying jaw toward the fixed anvil jaw by means of a pressure responsive clutch means. This provides an arrangement wherein the instrument closing and the establishment of the gap of the instrument are controlled by the pressure put upon the organ or tissue by the instrument. With prior art instruments, once the surgeon advanced the staple cartridge-carrying jaw to the predetermined position relative to the fixed anvil jaw, he could be assured that the gap therebetween was within the proper working gap of the instrument and its staples, assuring correct formation of the staple sutures. In the surgical stapling instrument of the present invention, since the closing of the instrument is controlled by the pressure applied to the organ or tissue to be sutured, the gap between the fixed jaw and the staple cartridge-carrying jaw may not fall within the range of the proper working gap of the instrument. As a consequence, the instrument of the present invention is provided with latch means which preclude movement of the staple driver actuator unless the gap of the instrument is within the limits of its proper working gap. Thus, if the gap established in response to the pressure being applied to the organ or tissue does not fall within the proper working gap of the instrument, use of the instrument is contraindicated. The pressure sensitive mechanism which controls the closure of the instrument has a positive drive to open the instrument. The staple driver actuator latch means also assures that the instrument is sequence controlled.

DISCLOSURE OF THE INVENTION

The surgical stapling instrument of the present invention comprises a fixed anvil jaw and a movable staple cartridge-carrying jaw. The staple cartridge contains a plurality of staple sutures and a driver therefore. The staple cartridge-carrying jaw is shiftable toward and away from the anvil jaw. The instrument is also provided with a staple driver actuator to activate the staple driver of the staple cartridge and to cause the staple sutures thereof to pass through the tissue or organ to be sutured. The tissue or organ is located between the anvil jaw and the staple cartridge of the staple cartridge-carrying jaw. The staples are clinched by grooves in the anvil jaw.

The staple cartridge-carrying jaw is shiftable toward and away from the fixed anvil jaw by means of a rotatable drive knob operatively connected to the staple cartridge-carrying jaw by a clutch means. The clutch means is positive acting during shifting of the staple cartridge-carrying jaw away from the fixed anvil jaw, but is pressure responsive when driving the staple cartridge-carrying jaw toward the fixed anvil jaw so as to effectively disengage the drive knob from the staple cartridge-carrying jaw when a predetermined pressure is applied to the organ or tissue to be sutured.

The staple driver actuator is shifted toward and away from the fixed anvil jaw by a wing nut-screw assembly. An automatic latch means is provided to preclude shifting of the staple driver actuator unless the gap between the staple cartridge-carrying jaw and the fixed anvil jaw (determined by the above mentioned clutch means) is within the limits of tne working gap of the instrument.

BRIEF DESCRIPTION OF THE DRAWINGS

FIG. 1 is a fragmentary elevational view of the instrument of the present invention.

FIG. 2 is a fragmentary elevational view of the instrument as seen from the left of FIG. 1.

FIG. 3 is a fragmentary elevational view of the instrument of FIG. 1 as seen from the right of that Figure.

FIG. 4 is a cross sectional view taken along section line 4—4 of FIG. 3.

FIG. 12 is a fragmentary cross sectional view taken along section line 12—12 of FIG. 11.

FIG. 13 is a fragmentary perspective view of the upper end of the staple driver actuator of the surgical instrument.

FIG. 14 is a cross sectional view taken along section line 14—14 of FIG. 4.

FIG. 15 is a cross sectional view taken along section line 15—15 of FIG. 14.

FIG. 16 is a side elevational view of the staple cartridge used with the surgical instrument of the present invention.

FIG. 17 is an end elevational view of the cartridge of FIG. 16 as seen from the right of that Figure.

FIG. 18 is a plan view of the staple cartridge of FIG. 16.

DETAILED DESCRIPTION OF THE INVENTION

Figure 5:
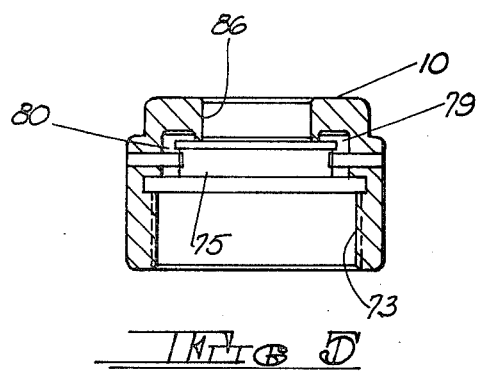
FIG. 5 is a cross sectional, elevational view of the instrument drive knob.

Reference is first made to FIGS. 1, 2 and 3 which illustrate the instrument of the present invention and in which like parts have been given like index numerals.

The instrument is generally indicated at 1 and comprises a body 2 having a front cover 3. The lower end of body 2 is C-shaped as at 4, providing a fixed jaw 5. The fixed jaw 5 has an anvil surface 6. While the anvil surface 6 may constitute a separate element affixed to and supported by the fixed jaw 5, for purposes of this exemplary showing, the anvil surface 6 is illustrated as being an integral, one-piece part of fixed jaw 5.

Shiftably mounted within the body 2 there is a movable staple cartridge-carrying jaw 7. The staple cartridge-carrying jaw supports a staple cartridge 8 provided with a plurality of staple sutures (not shown) and a staple driver 9 (see FIG. 2) for driving the staple sutures from the staple cartridge 8, through the tissue or organ to be sutured, and against the anvil surface 6 which clinches the staple sutures. The movable staple cartridge-containing jaw 7 is shiftable toward and away from the fixed jaw 5 by a drive knob 10 at the upper end of the instrument, as will be described hereinafter.

Shiftably mounted within the staple cartridge-carrying jaw 7 there is a staple driver actuator 11 (see FIG. 2). The staple driver actuator 11 is shiftable to activate staple driver 9 by a wing nut 12 at the upper end of the instrument, again as will be described in detail hereinafter.

Figure 10:
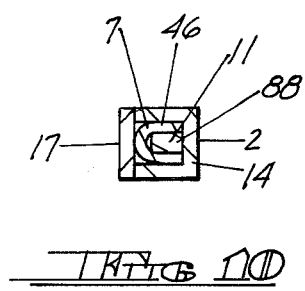
FIG. 10 is a cross sectional view taken along section line 10—10 of FIG. 4.

Reference is now made to FIG. 4. In FIG. 4 (as in all of the Figures) like parts have been given like index numerals. The upper portion 13 of body 2 is substantially semi-cylindrical (see FIG. 11). The body 2 has an intermediate elongated portion 14 of U-shaped cross section (see FIG. 10). The elongated portion 14 of body 2 terminates in the C-shaped portion 4 providing fixed jaw 5 and anvil surface 6. The free end of fixed jaw 5 is upturned as at 15.

Figure 11:
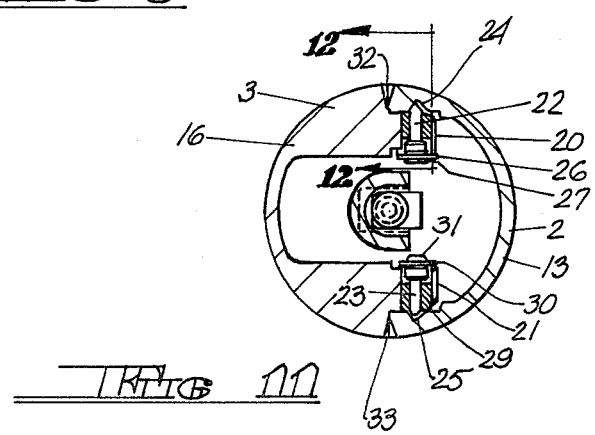
FIG. 11 is a cross sectional view taken along section line 11—11 of FIG. 4.

The front cover 3 of the instrument has an upper semi-cylindrical portion 16, similar to the portion 13 of body 2 see FIG. 11). Extending downwardly from the upper portion 16, the front cover 3 has an elongated flat portion 17 (see FIG. 10). The lowermost end of the portion 17 slopes downwardly and inwardly, as shown at 17a.

The front cover 3 is detachably mounted to the body 2. To this end, the body 2 is provided with a pair of spaced ears 18 and 19 which provide notches 18a and 19a adapted to receive the downwardly and inwardly sloped end 17a of front cover 3.

The upper portion 16 of front cover 3 has a pair of forwardly extending bosses 20 and 21 adapted to lie adjacent the inside surface of the upper portion 13 of body 2 and having latch pins 22 and 23 engaging notches 24 and 25, respectively, on the inside surface of the upper portion 13 of body 2.

Reference is made to FIGS. 11 and 12 wherein the boss 20 is shown. The boss 20 carries a resilient spring finger 26 affixed thereto by a rivet or pin means 27. The boss 20 also carries a bushing 28 in which the latch pin 22 is slidably mounted. The upper end of spring finger 26 rests against the head of latch pin 22 urging the pin to its latching position in notch 24.

As is evident from FIG. 11, the boss 21 and latch pin 23 constitute an arrangement which is identical to and a mirror image of the boss 20 and latch pin 22 arrangement. Thus, the pin 23 is mounted in a bushing 29 and is urged to its latching position by a spring member 30 held in place by rivet or pin 31.

To mount the front cover 3 on the body 2 it is only necessary to locate the lowermost portion 17a of the front cover in the notches 18a and 19a of ears 18 and 19. The front cover 3 is then pivoted thereabout toward the body 2. Bosses 20 and 21 will enter the body 2 and the latch pins 22 and 23 will be depressed against the action of their respective spring fingers 26 and 30 until the upper portion 16 of front cover 3 is fully seated against the upper portion 13 of body 2, at which time the latch pins 22 and 23 are free to enter their respective notches 24 and 25 in the upper portion 13 of body 2. At this point, the cover member 3 will be firmly held in place on the body 2.

Adjacent portions of the upper part 16 of front cover 3 and the upper part 13 of body 2 may be relieved so as to form notches 32 and 33 (see FIGS. 1 and 11). By insertion of an appropriate tool in one or both of the notches 32 and 33, the upper portion 16 of front cover 3 may be pried away from the upper portion 13 of body 2. The notches 24 and 25 on the interior surface of the upper portion 13 of body 2 are so configured that such a prying action will cause latch pins 22 and 23 to shift toward each other, against the action of their respective spring fingers 26 and 30, releasing front cover 3 from the body 2.

So that the movable staple cartridge-carrying jaw 7 may be better understood, reference is first made to FIGS. 16 through 18 wherein the staple cartridge 8 is shown. The cartridge comprises an elongated body having an upstanding portion 34 and a base portion 35 so as to be of inverted T-shaped cross section. The base portion 35 forms shoulders 36 and 37 to either side of the upstanding portion 34. Adjacent the shoulders 36 and 37 the upstanding portion 34 has a pair of longitudinal slots 38 and 39. It will be evident from FIG. 16 that the longitudinal slot 39 terminates short of the left hand end of the upstanding body portion 34 (as viewed in that Figure), as at 39. It will be understood that the slot 38 also terminates short of the left hand end of the upstanding portion 34 (as viewed in FIG. 16) in the same manner.

Figure 21:
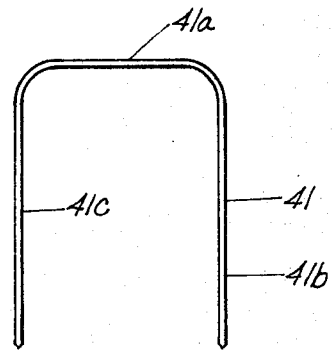
FIG. 21 is an elevational view of a staple suture of the type used with the surgical stapling instrument of the present invention, the surgical suture being illustrated in its uncrimped condition.

The upstanding portion 34 and base portion 35 of cartridge 8 have parallel rows of recesses therein, each recess containing a generally U-shaped wire staple suture. One row of such recesses is shown at 40 in FIG. 4, each containing a staple suture 41. An exemplary wire staple suture 41 is illustrated in FIG. 21. The other row of staple suture containing recesses (not shown) is staggered with respect to the recesses 40. This enables the provision of a single zig-zag shaped staple driver 9. The staple driver 9 has first segments 9a which overlie one row of staple sutures and second segments 9b overlying the second row of staple sutures. The staple driver 9 is shiftable downwardly into the body of staple cartridge 8 so as to drive the staple sutures therefrom, as will be described hereinafter.

While the staple cartridge has been illustrated in an embodiment having a single staple driver 9, staple cartridges are known having a separate driver for each row of staples and such a cartridge could be used in the instrument of the present invention. Furthermore, the instrument of the present invention is not limited to a staple cartridge containing two rows of staple sutures. Cartridges containing a single row of staple sutures or more than 2 rows of staple sutures can be used so long as the anvil surface 6 is provided with the correct number of staple clinching grooves, appropriately arranged, as will be discussed hereinafter.

Returning to FIG. 4, the movable staple cartridge-carrying jaw 7 has an inverted U-shaped portion 42 at its lowermost end. The U-shaped portion 42 has downwardly depending legs 43 and 44 (see FIG. 2) between which the cartridge 8 may be located. The lowermost ends of legs 43 and 44 rest upon staple cartridge shoulders 36 and 37, respectively. The inside surfaces of the legs 43 and 44 are provided with lugs not shown) adapted to extend into the staple cartridge grooves 38 and 39 so that the staple cartridge is locked in place within the staple cartridge-carrying jaw.

The legs 43 and 44 are slightly extended at that end of the U-shaped portion 42 of the staple cartridge-carrying jaw 7 adjacent the C-shaped portion 4 of body 2. The extended portion of leg 43 is shown at 43a in FIG. 4. The leg 44 has a similar extension (not shown). The portion 4 of the body 2 has a pair of parallel slots, one of which is shown at 45 in FIG. 4 to accommodate the extension 43a. The extension of leg 44 will be similarly accommodated in the other slot of the pair, not shown. This will assure that the staple cartridge-carrying jaw 7 and the staple cartridge 8 will be properly aligned with respect to fixed jaw 5 and anvil surface 6.

The staple cartridge-carrying jaw 7 has an intermediate portion 46 of C-shaped cross section which is slidably received in the intermediate portion 14 of body 2. This is most clearly shown in FIG. 10.

The uppermost portion 47 of staple cartridge-carrying jaw 7 is cylindrical and is externally threaded as at 48. The upper cylindrical portion 47 has a central threaded bore 49. The bore 49 leads into an upper coaxial bore 50 which is unthreaded and of slightly larger diameter. The uppermost end of portion 47 of the staple cartridge-carrying jaw 7 is provided with an upstanding annular flange 51 having a plurality of radial slots 52 formed therein. This is best shown in FIGS. 4 and 15. The purposes of threaded bore 49, bore 50, flange 51 and radial slots 52 will be described hereinafter.

Figure 25:
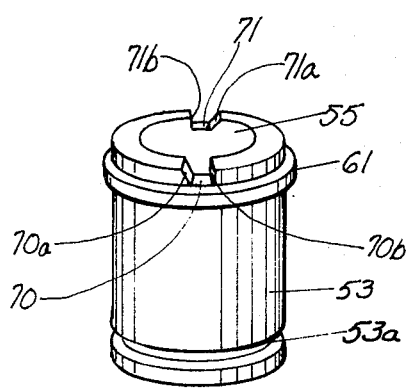
FIG. 25 is a perspective view of the drive nut of the surgical stapling instrument.

A cylindrical drive nut 53 is mounted in the upper portion 13 of body 2 and the upper portion 16 of front cover 3 (see FIGS. 4 and 25). The drive nut 53 has an annular groove 53a adapted to receive an annular rib 53b formed in both the upper portion 13 of body 2 and the upper portion 16 of front cover 3, thus permitting rotation of drive nut 53 while preventing axial shifting thereof with respect to the upper portion 13 of body 2 and the upper portion 16 of front cover 3. The drive nut 53 has a first axial bore 54 which is threaded and is threadedly engaged by the threads 48 of the upper portion 47 of the staple cartridge-carrying jaw 7. The threaded bore 54 leads to a second unthreaded axial bore 55 in drive nut 53. The bore 55 is of slightly larger diameter and is adapted to accommodate the lower end of wing nut 12, as will be described hereinafter.

The drive nut 53 is surrounded by a thrust bearing 56 which rests upon the upper ends of body portion 13 and front cover portion 16. Thrust bearing 56, in turn, is surmounted by retainer ring 57. Retainer ring 57 has a first axial bore 58 of such diameter as to just nicely receive the drive nut 53. Retainer ring 57 has a second axial bore 59 of larger diameter, forming a shoulder 60 therebetween. Drive nut 53 has an annular rib 61 which abuts the retainer ring shoulder 60.

Figure 6:
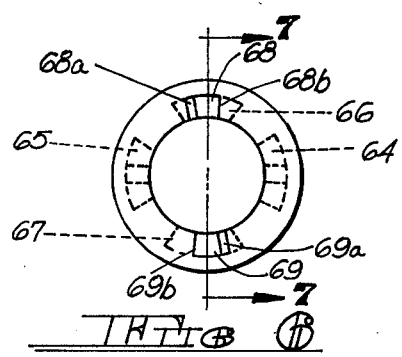
FIG. 6 is a bottom view of the clutch plate of the instrument.
Figure 7:
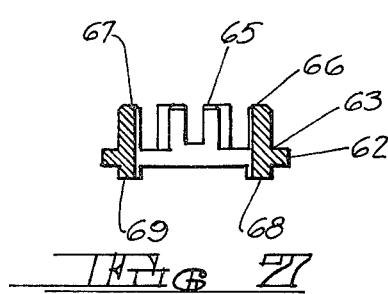
FIG. 7 is a cross sectional view taken along section line 7—7 of FIG. 6.
Figure 8:
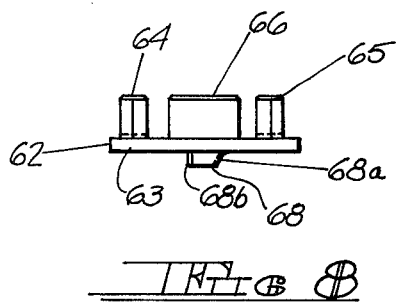
FIG. 8 is a side elevational view of the clutch plate of FIGS. 6 and 7.

Within retainer ring 57 and resting upon the upper end of drive nut 53 there is a clutch plate 62. The clutch plate is most clearly shown in FIGS. 6, 7 and 8. The clutch plate 62 has an annular body 63 of an exterior diameter to be just nicely received within retainer ring 57 (see FIG. 4). The upper surface of the body has four upstanding spacing elements arranged in diametrically opposed pairs 64–65 and 66–67. The spacing elements 64 and 65 are bifurcated for purposes to be taught hereinafter.

The lower surface of the clutch plate body 63 carries at least one drive tooth. For purposes of an exemplary showing, the clutch plate is illustrated as being provided with a diametrically opposed pair of identical drive teeth 68 and 69. Drive tooth 68 has a front surface 68a which slopes forwardly and upwardly and a vertical rear surface 68b. Drive tooth 69 has a similar sloping forward surface 69a and a vertical rear surface 69b.

As indicated above and as shown in FIG. 4, the clutch plate 62 is adapted to lie on the uppermost surface of drive nut 53. Reference is again made to FIG. 25 which is a perspective view of drive nut 53. It will be noted that the upper edge of the drive nut is provided with a pair of diametrically opposed notches 70 and 71, the configuration of which corresponds to the configuration of drive teeth 68 and 69. Thus, notch 70 has an upwardly and outwardly sloping front surface 70a and a vertical rear surface 70b while notch 71 has an upwardly and outwardly sloping front surface 71a and a vertical rear surface 71b. The notches 70 and 71 will accommodate either of the drive teeth 68 and 69, as will be apparent hereinafter.

Reference is now made to FIGS. 4 and 5. The instrument of the present invention is provided with a drive knob 10, as stated above. The drive knob 10 is a hollow cylindrical element having a first internally threaded portion 73 adapted to cooperate with the exterior surface of retainer ring 57 which is threaded as at 74. The drive knob has a second portion 75 having an internal diameter to just nicely receive the upstanding spacing elements 64 through 67 of clutch plate 62 (see FIG. 4). As is clearly shown in FIGS. 4 and 9, the portion 75 of drive knob 10 is provided with a pair of diametrically opposed pins 76 and 77, the ends of which extend into the interior of the drive knob. The pins 76 and 77 are so located as to engage the bifurcated upstanding spacer elements 64 and 65 of clutch plate 62. This assures that as the drive knob 10 is rotated, the clutch plate 62 will rotate with it.

Figure 9:
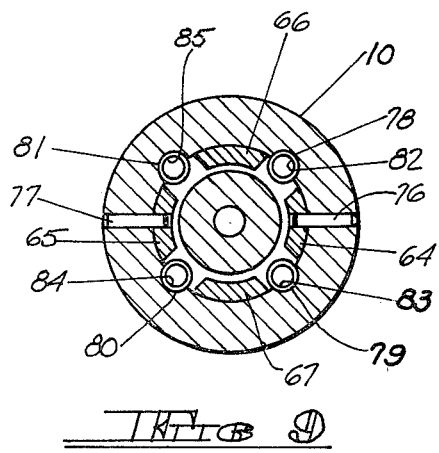
FIG. 9 is a cross sectional view taken along section line 9—9 of FIG. 4.

The interior portion 75 of drive knob 10 is also provided with four evenly spaced recesses 78 through 81 which are shown in FIG. 9 and two of which are shown in FIG. 5. These recesses are adapted to accommodate four compression springs 82 through 85, respectively. The upper ends of compression springs 82 through 85 abut the upper inside surface of drive knob 10. The lower ends of springs 82 through 85 abut the body portion 63 of clutch plate 62 between the upstanding spacer elements 64 through 67. As a consequence, the compression springs 82 through 85 yieldably urge the clutch plate 62 against the upper end of drive nut 53. Finally, drive knob 10 has an axial bore portion 86 (see FIG. 4 and 5) so sized as to rotatively receive wing nut 12.

The staple driver actuator 11 is most clearly shown in FIG. 4. The staple driver actuator 11 is shiftably mounted within the staple cartridge-carrying jaw 7 and has at its lower end a portion 87 which extends longitudinally above staple cartridge 8 and staple driver 9. As will be described hereinafter, it is the portion 87 which contacts staple driver 9 to drive the staple sutures 41 from the cartridge, through the organ or tissue to be sutured, and against anvil surface 6. The staple driver actuator 11 has an elongated portion 88 which extends longitudinally within the intermediate portion 46 of staple cartridge-carrying jaw 7 (see FIG. 10).

The uppermost end of the staple driver actuator 11 is provided with a transverse slot 89 and a vertical slot 90 forming bifurcations 91 and 92 (see FIG. 13). The slot 89 is adapted to receive the head 93 and the slot 90 is adapted to receive the neck 94 of a screw 95. The screw 95 is threadedly engaged in the threaded bore 49 of the upper portion 47 of the staple cartridge-carrying jaw 7. This is clearly shown in FIG. 4. The screw 95 is operatively connected to wing nut 12. It will be understood that rotation of wing nut 12 will, by virtue of the threaded engagement between screw 95 and the upper end 47 of the staple cartridge-carrying jaw 7 (and by virtue of the rotatable connection of screw 95 with non-rotatable staple driver actuator 11) result in axial shifting of the staple driver actuator 11. The portion 88 of staple driver actuator 11 is provided with a notch 88a. The limit pin 88b extends transversely of notch 88a with its ends mounted in coaxial bores not shown) in the intermediate portion 46 of staple cartridge-carrying jaw 7. The pin 88b limits the travel of staple driver actuator 11.

Wing nut 12 is provided with a bore 96 adapted to accommodate the uppermost end of screw 95. As will be evident from FIG. 14, the upper end of screw 95 is slotted as at 97 and the lower end of wing nut 12 is slotted as at 98. Located within slots 97 and 98 is a latch 99. A pin 100 passes through the lower slotted end of wing nut 12, the upper slotted end of screw 95 and latch 99. Thus, pin 100 not only attaches the upper end of screw 95 to the lower end of wing nut 12, but also pivotally mounts latch 99 in screw slot 97 and wing nut slot 98. A second pin 101 (see FIGS. 4 and 14) passes through the lower end of wing nut 12 and perforation 102 in latch 99. The perforation 102 is of a larger diameter than the diameter of pin 101 and cooperates with pin 101 to limit the amount of pivoting of latch 99 about pin 100.

Referring particularly to FIG. 4, the latch 99 has a nose portion 103 which, when the gap between fixed jaw 5 and staple cartridge-carrying jaw 7 is within the proper working gap of the instrument, will contact beveled surface 104 on drive nut 53. A spring 105 is provided with one end mounted in a perforation 106 of wing nut 12 and the other end wrapped about latch 99 in such a way that the latch is urged to pivot about pin 100 in a clockwise direction as viewed in FIG. 4. This will assure that the latch nose 103 will remain in contact with surface 104 when the proper working gap of the instrument is achieved. If the gap between the staple cartridge-carrying jaw 7 and fixed jaw 5 is greater than the proper working gap, the nose 103 of latch 99 will be opposite the inside surface of clutch plate 62 and, under the urging of spring 105 and within the limits permitted by pin 101 and perforation 102, the latch will shift in a clockwise direction (as viewed in FIG. 4) entering one of the notches 52 in the upper annular portion 51 of staple cartridge-carrying jaw 7. Thus, the latch 99 will preclude rotation of wing nut 12 and screw 95, thereby preventing shifting of staple driver actuator 11 to actuate staple driver 9. Alternatively, if too small a working gap is achieved by the surgeon, the nose portion 103 of latch 99 will contact the inside surface 55 of drive nut 53. This will cause a counter-clockwise rotation of latch 99 about pin 100 within the limits dictated by pin 101 and latch perforation 102 and against the action of spring 105. Such counter-clockwise rotation of latch 99 will also cause it to enter one of the slots 52 in the upper annular portion 51 of staple cartridge-carrying jaw 7. This again will preclude turning of wing nut 12 and advancement of staple driver actuator 11 against staple driver 9.

Figure 19:
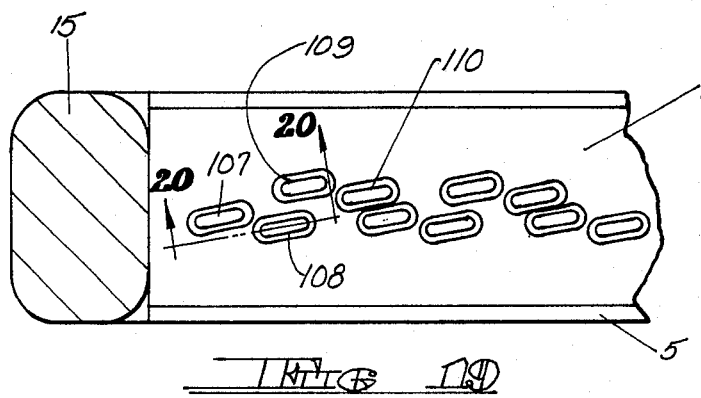
FIG. 19 is a fragmentary cross sectional view taken along section line 19—19 of FIG. 4.
Figure 20:
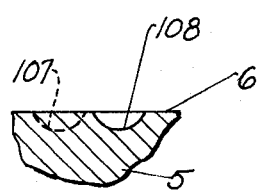
FIG. 20 is a fragmentary cross sectional view taken along section line 20—20 of FIG. 19.

Reference is now made to FIGS. 19 through 24. FIG. 19 is a fragmentary view taken along section line 19—19 of FIG. 4 illustrating the anvil surface 6 on fixed jaw 5. The anvil surface 6 is provided with a plurality of clinching grooves which clinch the legs of the staple sutures when the staple sutures are driven from the staple cartridge 8, through the organ or tissue to be sutured, and into the clinching grooves. The anvil surface 6 is provided with a pair of clinching grooves for each staple suture. One such pair is shown at 107 and 108. Another pair of clinching grooves is shown at 109 and 110. From the relative positions of the pairs 107-108 and 109-110 it will be noted that the staple suture to be clinched by clinching grooves 109 and 110 lies in a different row and is staggered with respect to the staple suture to be clinched by clinching grooves 107 and 108. The configuration of clinching grooves 107 and 108 is clearly shown in FIG. 20.

Figure 22:
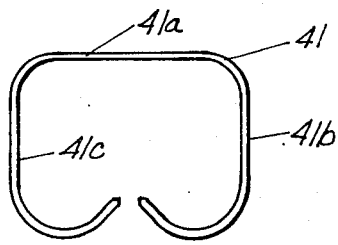
FIG. 22 is an elevational view of the staple suture of FIG. 21 illustrated in its crimpled condition when the gap of the instrument is at the upper limit of the proper working gap.
Figure 23:
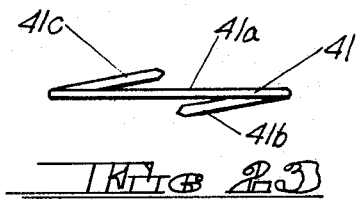
FIG. 23 is a plan view of the staple suture of FIG. 22.
Figure 24:
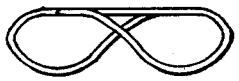
FIG. 24 is an elevational view of the staple suture of FIG. 21 in its crimped condition when the gap of the instrument is at the maximum lower limit of the proper working gap.

FIG. 21 illustrates an exemplary wire staple suture 41 having a crown portion 41a and downwardly depending legs 41b and 41c. FIG. 22 illustrates the staple suture of FIG. 21 after having been clinched by clinching grooves 107 and 108 when the gap between the staple cartridge-carrying jaw 7 and fixed jaw 5 is at the maximum proper working gap of the instrument. Since the clinching grooves 107 and 108 lie at an angle to the long axis of anvil surface 6 and the long axis of the staple cartridge 8, the legs 41b and 41c of staple suture 41 will not only be clinched as shown in FIG. 22 but will be slightly twisted (as shown in FIG. 23) so as to lie to either side of crown portion 41a. FIG. 24 illustrates the staple of FIG. 21 in its formed condition when the gap between the staple cartridge-carrying jaw 7 and the fixed jaw 5 is at the minimum proper working gap of the instrument.

The various elements of instrument 1 having been described in detail, the operation of the instrument 1 may be set forth as follows. When the instrument is ready for use, the U-shaped portion 42 of the staple cartridge-carrying jaw 7 will be provided with a staple cartridge and the jaw 7 will be in a retracted position, i.e. at its maximum distance from fixed jaw 5. The staple driver actuator 11 will also be in its fully retracted position with respect to the staple cartridge-carrying jaw 7. The organ or tissue to be sutured is located between fixed jaw 5 and staple cartridge-carrying jaw 7. The staple cartridge-carrying jaw 7 is then advanced toward fixed jaw by the surgeon. This is accomplished by clockwise rotation of drive knob 10. Drive knob 10 transmits the rotative force to clutch plate 62 by means of pins 76 and 77. The clutch plate 62, having drive teeth 68 and 69 engaged in notches 70 and 71 under the force supplied by compression springs 82 through 85, will cause rotation of drive nut 53. Since the staple cartridge-carrying jaw is non-rotatively mounted in the instrument body 2 and since its upper end 48 is threadedly engaged by drive nut 53, the rotation of the drive nut 53 will cause the staple cartridge-carrying jaw 7 to advance toward fixed jaw 5 and against the tissue or organ being sutured. This will continue until the resistance of the organ or tissue to compression exceeds the torque limits of clutch plate 62 and springs 82 through 85. At this point, clutch plate 62 will disengage from drive nut 53, the sloping surfaces 68a and 69a of drive teeth 68 and 69 riding up and over the sloping surfaces 70a and 71a of notches 70 and 71. As a result, continued rotation of drive knob 10 will not further advance staple cartridge-containing jaw 7 toward fixed jaw 5, but will result in a ratcheting noise signaling that the clutch plate 62 is disengaged from drive nut 53. This arrangement establishes a gap between the staple cartridge-carrying jaw 7 and fixed jaw 5 controlled by the pressure they apply to the organ or tissue located therebetween.

The staple driver actuator 11 should initially be in its fully retracted position as illustrated in FIG. 4. If the gap between staple cartridge-carrying jaw 7 and fixed jaw 5 (as established by the compressive force on the organ or tissue to be sutured) falls within the proper working gap of the instrument, the latch 99 will be in the position illustrated in FIG. 4. With the latch 99 in this position, the wing nut 12 may be rotated in a clockwise direction which will result in rotation of screw 95. Rotation of screw 95 will cause axial shifting of the staple driver actuator 11 into contact with staple driver 9. Continued rotation of wing nut 12 will cause the staple driver 9 to drive the staple sutures 41 through the organ or tissue being sutured and into the clinching grooves of anvil surface 6, resulting in clinching of the staple sutures somewhere at or between the minimum safe clinching illustrated in FIG. 22 (where the gap is at its safe maximum) and the maximum clinching as illustrated in FIG. 24 (where the gap is at its safe minimum).

As indicated above, if the closing of the staple cartridge-carrying jaw 7 toward fixed jaw 5 (by means of the pressure responsive clutch plate described above) has provided a gap which exceeds the maximum proper working gap of the instrument, the nose portion 103 of latch 99 will be located opposite the interior surface of clutch plate 62 which will permit the latch 99 to rotate under the influence of spring 105 into one of the grooves 52 of the uppermost annular flange 51 on the staple cartridge-carrying jaw 7. This will preclude advancement of the staple driver actuator 11 and will indicate to the surgeon that the instrument of the present invention should not be used. Similarly, if the gap established in response to the pressure applied to the tissue or organ to be sutured is smaller than the minimum proper working gap of the instrument 1, the latch nose 103 will contact the inside surface 55 of drive nut 53 causing the latch to be shifted in a counterclockwise direction, against the influence of spring 105, and into one of the grooves 52. This will also preclude advancement of the staple driver actuator 11, again contraindicating use of the instrument 1.

When the gap established in response to the pressure applied to the tissue or organ to be sutured does fall within the proper working gap of instrument 1 and the staple driver actuator 11 has been advanced by wing nut 12 to implant and properly clinch the double row of staples 41, the surgeon then rotates the drive knob 10 in a counter-clockwise direction, retracting staple cartridge-carrying jaw 7 away from fixed jaw 5. This permits easy removal of the instrument 1 from the now sutured organ or tissue. When the drive knob 10 is rotated in a counter-clockwise direction, the vertical surfaces 68b and 69b of drive teeth 68 and 69 will cooperate with the vertical surfaces 70b and 71b of notches 70 and 71. As a result, the coaction of clutch plate 62 and drive nut 53 is always positive to retract the staple cartridge-carrying jaw.

Modifications may be made in the invention without departing from the spirit of it.

What is claimed is:

1. In a surgical stapling instrument of the type having a fixed jaw with an anvil surface thereon with staple clinching grooves therein, a movable jaw shiftable toward and away from said fixed jaw and carrying a plurality of staples and a driver therefor, means to shift said movable jaw, a staple driver actuator shiftable between a retracted position and an advanced position wherein it actuates said staple driver to cause said staples to pass through tissue located between said fixed jaw and said movable jaw and to be clinched by said anvil surface, and means to shift said staple driver actuator, said surgical stapling instrument having a working gap comprising a range of distances between said fixed jaw and said movable jaw throughout which said staples can be properly implanted and clinched, the improvement comprising latch means permitting shifting of said staple driver 2. The structure claimed in claim 1 wherein said surgical stapling instrument comprises an elongated hollow body having an intermediate portion, a rearward end and a forward end terminating in said fixed jaw, an elongated shank terminating at its forward end in said movable jaw and at its rearward end in a cylindrical portion, said shank being mounted in said hollow instrument body so as to be non-rotatable therein and to be axially shiftable therein by said movable jaw shifting means, a staple driver actuator shank mounted within said movable jaw shank and being axially shiftable and non-rotatable therein, the forward end of said staple driver actuator shank terminating in said staple driver actuator, the rearward end of said staple driver actuator shank terminating short of said cylindrical rearward end of said movable jaw shank, said cylindrical rearward end of said movable jaw shank having an axial bore extending therethrough, a first portion of said bore being threaded and a second portion of said bore near the rearwardmost end of said movable jaw shank being unthreaded and of slightly larger diameter, an elongated rod-like screw having a forward end followed by a threaded portion and an unthreaded portion terminating in a rearward end of said screw, the forward end of said screw being rotatably attached to said rearward end of said staple driver actuator shank, said screw being located in said bore of said cylindrical rearward end of said movable jaw shank with its threaded portion threadedly engaged in said threaded portion of said last mentioned bore, said unthreaded portion of said screw being partially located within said last mentioned bore and extending rearwardly beyond said rearward end of said movable jaw shank, a wing nut having a forward cylindrical portion rotatably and axially shiftably mounted at said rearward end of said instrument, said forward cylindrical portion of said wing nut having an axial bore therein, said rearward end of said screw being located within said wing nut bore and being non-rotatably affixed therein, whereby rotation of said wing nut in a first direction will result in rotation of said screw in said internally threaded portion of said movable jaw cylindrical rearward end to shift said staple driver via its shank toward said retracted position thereof and rotation of said wing nut in a second direction will cause rotation of said screw in said internally threaded portion of said movable jaw cylindrical rearward end to shift said staple driver actuator via its shank toward said advanced position thereof.

3. The structure claimed in claim 1 wherein each of said staples is of inverted U-shaped configuration having a crown portion and a pair of downwardly depending legs, said anvil surface staple clinching grooves being arranged in pairs, each pair adapted to receive and clinch the legs of one of said staples, said clinching grooves of each pair lying at an angle to the long axis of said anvil surface whereby said legs of each staple, when clinched, will be slightly twisted so as to lie to either side of their respective staple crown portion.

4. The structure claimed in claim 2 wherein said rearward end of said screw and said forward cylindrical end of said wing nut are slotted, a latch located in said slots, a pin extending through transverse coaxial perforations in said rearward end of said screw, said forward end of said wing nut and said latch non-rotatably affixing said screw to said wing nut and pivotally mounting said latch in said slots, said rearward cylindrical end of said movable jaw shank having an annular flange thereon surrounding said screw and having a plurality of radial notches formed therein, said latch being pivotable between first and second positions in engagement with one of said radial notches wherein it will prevent rotation of said wing nut and said screw to prevent shifting of said staple driver actuator to said advanced position and an intermediate third position out of engagement with said radial notches wherein it will permit rotation of said wing nut and said screw to shift said staple driver actuator to said advanced position thereof, and means to shift said latch from one of said first and second positions to said third position only when said gap between said movable jaw and said fixed jaw falls within said working gap of said surgical stapling instrument.

5. The structure claimed in claim 4 werein said shifting means for said latch comprises a laterally extending nose on said latch, said instrument having a first surface contactable by said nose to maintain said latch in said first position when said gap between said fixed and movable jaws exceeds said working gap, said instrument having a second surface contactable by said nose to maintain said latch in said second position when said gap between said fixed and movable jaws is less than said working gap, said instrument having a third surface between said first and second surfaces, said third surface being contactable by said nose to maintain said latch in said intermediate third position when said gap between said fixed and movable jaws falls within said working gap.

6. In a surgical stapling instrument of the type having a fixed jaw with an anvil surface thereon with staple clinching grooves therein, a movable jaw shiftable toward and away from said fixed jaw and carrying a plurality of staples and a driver therefor, means to shift said movable jaw, a staple driver actuator shiftable between a retracted position and an advanced position wherein it actuates said staple driver to cause said staples to pass through tissue located between said fixed jaw and said movable jaw and to be clinched by said anvil grooves, and means to shift said staple driver actuator, said surgical stapling instrument having a working gap comprising a range of distances between said fixed jaw and said movable jaw throughout which said staples can be properly implanted and clinched, the improvement comprising means operatively connecting said movable jaw and said movable jaw shifting means to shift said movable jaw away from said fixed jaw and to advance said movable jaw toward said fixed jaw to establish a gap therebetween in accordance with a predetermined pressure applied by said jaws to said tissue therebetween, and latch means permitting shifting of said staple driver actuator by said staple driver actuator shifting means only when said established gap falls within said working gap of said instrument.

7. The structure claimed in claim 6 wherein said surgical instrument comprises an elongated hollow body having an intermediate portion, a rearward end and forward end terminating in said fixed jaw extending perpendicularly to the long axis of said instrument body, a hollow, cylindrical, drive nut captively and rotatably mounted at said rearward end of said instrument body, said drive nut having forward and rearward ends, the interior surface of said drive nut being threaded from said forward end of said drive nut to a point short of said rearward end of said drive nut, the remainder of said interior surface being unthreaded, said drive nut being non-shiftable axially with respect to said instrument body, a rearward portion of said drive nut extending beyond said rearward end of said instrument body, an elongated shank terminating at its forward end in said movable jaw and at its rearward end in an externally threaded cylindrical portion, said shank being mounted in said hollow instrument body so as to be axially shiftable and non-rotatable therein, said externally threaded cylindrical rearward end of said movable jaw shank being threadedly engaged in said drive nut, an externally threaded retainer ring mounted at said rearward end of said instrument body about said rearward portion of said drive nut extending beyond said instrument body rearward end, a clutch plate located within said retainer ring, said clutch plate having a first side facing and located adjacent said rearward end of said drive nut, a hollow internally threaded drive knob threadedly engaged on said retainer ring and operatively connected to said clutch plate such that rotation of said drive knob will cause rotation of said clutch plate, yieldable means urging said clutch plate into driving engagement with said rearward end of said drive nut such that rotation of said drive knob in a first direction will impart similar rotation to said clutch plate and said drive nut resulting in shifting of said movable jaw and its shank away from said fixed jaw and rotation of said drive knob in a second direction will impart similar rotation to said clutch plate and said drive nut to advance said movable jaw and its shank toward said fixed jaw until said predetermined pressure is achieved at which point said yieldable means will no longer maintain said clutch plate in driving engagement with said drive nut thus setting said clutch-established gap.

8. The structure claimed in claim 6 wherein each of said staples is of inverted U-shaped configuration having a crown portion and a pair of downwardly depending legs, said anvil surface staple clinching grooves being arranged in pairs, each pair adapted to receive and clinch the legs of one of said staples, said clinching grooves of each pair lying at an angle to the long axis of said anvil surface whereby said legs of each staple, when clinched, will be slightly twisted so as to lie to either side of their respective staple crown portion.

9. The structure claimed in claim 7 including at least one drive tooth on said first side of said clutch plate, said at least one tooth having a first drive surface perpendicular to said clutch plate, said at least one drive tooth having a second drive surface facing in said second direction and sloping in said second direction toward said clutch plate, said rearward end of said drive nut having at least one notch for said at least one clutch plate drive tooth, said at least one notch having first and second drive surfaces corresponding to and similarly shaped to said first and second drive surfaces of said at least one drive tooth, whereby when said drive knob is rotated in said first direction said perpendicular first drive surfaces of said at least one clutch drive tooth and said at least one drive nut notch will cooperate to shift said movable jaw away from said fixed jaw, and when said drive knob is rotated in said second direction said sloping second drive surfaces of said at least one clutch drive tooth and said at least one drive nut notch will cooperate to shift said movable jaw toward said fixed jaw until said predetermined pressure is achieved whereupon said sloping second drive surfaces of said at least one clutch drive tooth and said at least one drive nut notch will cooperate to shift said at least one drive tooth out of said at least one notch against the influence of said yieldable means, disengaging said clutch plate from said drive nut and thus setting said clutch-established gap.

10. The structure claimed in claim 7 including a plurality of upstanding spaced lugs on said second side of said clutch plate, a diametrically opposed pair of said lugs being bifurcated, a pair of diametrically opposed pins being mounted in said hollow drive knob and extending radially inwardly thereof, said pins being located between said bifurcations of said pair of clutch plate lugs, whereby rotation of said drive knob will be imparted to said clutch plate by the cooperation of said pins and said bifurcations and said clutch plate and said drive knob can independently shift axially.

11. The structure claimed in claim 7 wherein said yieldable means comprises a plurality of springs, one end of each of said springs being located in a socket formed therefor in the interior of said hollow drive knob, the other end of each of said springs abutting said second side of said clutch plate.

12. The structure claimed in claim 7 including a staple driver actuator shank mounted within said movable jaw shank and being axially shiftable and non-rotatable therein, the forward end of said staple driver actuator shank terminating in said staple driver actuator located within said movable jaw, the rearward end of said staple driver actuator shank terminating short of said cylindrical rearward end of said movable jaw shank, said cylindrical rearward end of said movable jaw shank having an axial bore extending therethrough, a first portion of said bore being threaded and a second portion of said bore near the rearwardmost end of said movable jaw shank being unthreaded and of slightly larger diameter, an elongated rod-like screw having a forward end followed by a threaded portion and an unthreaded portion terminating in a rearward end of said screw, the forward end of said screw being rotatably attached to said rearward end of said staple driver actuator shank, said screw being located in said bore of said cylindrical rearward end of said movable jaw shank with its threaded portion threadedly engaged in said threaded portion of said last mentioned bore, said unthreaded portion of said screw being partially located within said last mentioned bore and extending rearwardly beyond said rearward end of said movable jaw shank, a wing nut having a forward cylindrical portion rotatably mounted and axially shiftable in coaxial perforations in said drive knob, said clutch plate and said unthreaded portion of said hollow drive nut, said forward cylindrical portion of said wing nut having an axial bore therein, said rearward end of said screw being located within said wing nut bore and being non-rotatably affixed therein, whereby rotation of said wing nut in a first direction will result in rotation of said screw in said internally threaded portion of said movable jaw cylindrical rearward end to shift said staple driver actuator via its shank toward said retracted position thereof and rotation of said wing nut in a second direction will cause rotation of said screw in said internally threaded portion of said movable jaw cylindrical rearward end to shift said staple driver actuator via its shank toward said advanced position thereof.

13. The structure claimed in claim 12 wherein said rearward end of said screw and said forward cylindrical end of said wing nut are slotted, a latch located in said slots, a pin extending through transverse coaxial perforations in said rearward end of said screw, said forward end of said wing nut and said latch non-rotatably affixing said screw to said wing nut and pivotally mounting said latch in said slots, said rearward cylindrical end of said movable jaw shank having an annular flange thereon surrounding said screw and having a plurality of radial notches formed therein, said latch being pivotable between first and second positions in engagement with one of said radial notches wherein it will prevent rotation of said wing nut and said screw to prevent shifting of said staple driver actuator to said advanced position and an intermediate third position out of engagement with said radial notches wherein it will permit rotation of said wing nut and said screw to shift said staple driver actuator to said advanced position thereof, and means to shift said latch from one of said first and second positions to said third position only when said clutch-established gap falls within said working gap of said surgical stapling instrument.

14. The structure claimed in claim 13 wherein said shifting means for said latch comprises a laterally extending nose on said latch, said nose being located to contact the inside surface of said perforation in said clutch plate to maintain said latch in said first position when said clutch-established gap exceeds said working gap, said nose being locating to contact said unthreaded interior surface of said drive nut to maintain said latch in said second position when said clutch-established gap is less than said working gap, said unthreaded interior surface of said drive nut terminating in a narrow annular flared interior surface at said rearward end of said drive nut, said latch nose contacting said flared interior surface to maintain said latch in said intermediate third position when said clutch-established gap falls within said working gap.

15. The structure claimed in claim 14 including at least one drive tooth on said first side of said clutch plate, said at least one drive tooth having a first drive surface perpendicular to said clutch plate, said at least one drive tooth having a second drive surface facing in said second direction and sloping in said second direction toward said clutch plate, said rearward end of said drive nut having at least one notch for said at least one clutch plate drive tooth, said at least one notch having first and second drive surfaces corresponding to and similarly shaped to said first and second drive surfaces of said at least one drive tooth, whereby when said drive knob is rotated in said first direction said perpendicular first drive surfaces of said at least one clutch drive tooth and said at least one drive nut notch will cooperate to shift said movable jaw away from said fixed jaw, and when said drive knob is rotated in said second direction said sloping second drive surfaces of said at least one clutch drive tooth and said at least one drive nut notch will cooperate to shift said movable jaw toward said fixed jaw until said predetermined pressure is achieved whereupon said sloping second drive surfaces of said at least one clutch drive tooth and said at least one drive nut notch will cooperate to shift said at least one drive tooth out of said at least one notch against the influence of said yieldable means, disengaging said clutch plate from said drive nut and thus setting said clutch-established gap.

16. The structure claimed in claim 15 including a plurality of upstanding spaced lugs on said second side of said clutch plate, a diametrically opposed pair of said lugs being bifurcated, a pair of diametrically opposed pins being mounted in said hollow drive knob and extending radially inwardly thereof, said pins being located between said bifurcations of said pair of clutch plate lugs, whereby rotation of said drive knob will be imparted to said clutch plate by the cooperation of said pins and said bifurcations and said clutch plate and said drive knob can independently shift axially.

17. The structure claimed in claim 16 wherein said yieldable means comprises a plurality of springs, one end of each of said springs being located in a socket formed therefor in the interior of said hollow drive knob, the other end of each of said springs abutting said second side of said clutch plate.

18. In a surgical stapling instrument of the type having a fixed jaw with an anvil surface thereon with staple clinching grooves therein, a movable jaw shiftable toward and away from said fixed jaw and carrying a plurality of staples and a driver therefor, means to shift said movable jaw, a staple driver actuator shiftable between a retracted position and an advanced position wherein it actuates said staple driver to cause said staples to pass through tissue located between said fixed jaw and said movable jaw and to be clinched by said anvil grooves, and means to shift said staple driver actuator, the improvement comprising clutch means operatively connecting said movable jaw and said movable jaw shifting means to shift said movable jaw away from said fixed jaw and to advance said movable jaw toward said fixed jaw to establish a gap therebetween in accordance with a predetermined pressure applied by said jaws to said tissue therebetween.

19. The structure claimed in claim 18 wherein said surgical instrument comprises an elongated hollow body having and intermediate portion, a rearward end and a forward end terminating in said fixed jaw extending perpendicularly to the long axis of said instrument body, a hollow cylindrical drive nut captively and rotatably mounted at said rearward end of said instrument body, said drive nut having forward and rearward ends, the interior surface of said drive nut being threaded from said forward end of said drive nut to a point short of said rearward end of said drive nut, the remainder of said interior surface being unthreaded, said drive nut being non-shiftable axially with respect to said instrument body, a rearward portion of said drive nut extending beyond said rearward end of said instrument body, an elongated shank terminating at its forward end in said movable jaw and at its rearward end in an externally threaded cylindrical portion, said shank being mounted in said hollow instrument body so as to be axially shiftable and non-rotatable therein, said externally threaded cylindrical rearward end of said movable jaw shank being threadedly engaged in said drive nut, an externally threaded retainer ring mounted at said rearward end of said instrument body about said rearward portion of said drive nut extending beyond said instrument body rearward end, a clutch plate located within said retainer ring, said clutch plate having a first side facing and located adjacent said rearward end of said drive nut, a hollow internally threaded drive knob threadedly engaged on said retainer ring and operatively connected to said clutch plate such that rotation of said drive knob will cause rotation of said clutch plate, yieldable means urging said clutch plate into driving engagement with said rearward end of said drive nut such that rotation of said drive knob in a first direction will impart similar rotation to said clutch plate and said drive nut resulting in shifting of said movable jaw and its shank away from said fixed jaw and rotation of said drive knob in a second direction will impart similar rotation to said clutch plate and said drive nut to advance said movable jaw and its shank toward said fixed jaw until said predetermined pressure is achieved at which point said yieldable means will no longer maintain said clutch plate in driving engagement with said drive nut thus setting said clutch-established gap.

20. The structure claimed in claim 18 wherein each of said staples is of inverted U-shaped configuration having a crown portion and a pair of downwardly depending legs, said anvil surface staple clinching grooves being arranged in pairs, each pair adapted to receive and clinch the legs of one of said staples, said clinching grooves of each pair lying at an angle to the long axis of said anvil surface whereby said legs of each staple, when clinched, will be slightly twisted so as to lie to either side of their respective staple crown portion.

21. The structure claimed in claim 19 including at least one drive tooth on said first side of said clutch plate, said at least one drive tooth having a first drive surface perpendicular to said clutch plate, said at least one drive tooth having a second drive surface facing in said second direction and sloping in said second direction toward said clutch plate, said rearward end of said drive nut having at least one notch for said at least one clutch plate drive tooth, said at least one notch having first and second drive surfaces corresponding to and similarly shaped to said first and second drive surfaces of said at least one drive tooth, whereby when said drive knob is rotated in said first direction said perpendicular first drive surfaces of said at least one clutch drive tooth and said at least one drive nut notch will cooperate to shift said movable jaw away from said fixed jaw, and when said drive knob is rotated in said second direction said sloping second drive surfaces of said at least one clutch drive tooth and said at least one drive nut notch will cooperate to shift said movable jaw toward said fixed jaw until said predetermined pressure is achieved whereupon said sloping second drive surfaces of said at least one clutch drive tooth and said at least one drive nut notch will cooperate to shift said at least one drive tooth out of said at least one notch against the influence of said yieldable means, disengaging said clutch plate from said drive nut and thus setting said clutch-established gap.

22. The structure claimed in claim 19 including a plurality of upstanding spaced lugs on said second side of said clutch plate, a diametrically opposed pair of said lugs being bifurcated, a pair of diametrically opposed pins being mounted in said hollow drive knob and extending radially inwardly thereof, said pins being located between said bifurcations of said pair of clutch plate lugs, whereby rotation of said drive knob will be imparted to said clutch plate by the cooperation of said pins and said bifurcations and said clutch plate and said drive knob can independently shift axially.

23. The structure claimed in claim 19 wherein said yieldable means comprises a plurality of springs, one end of each of said springs being located in a socket formed therefor in the interior of said hollow drive knob, the other end of each of said springs abutting said second side of said clutch plate.

24. The structure claimed in claim 21 including a plurality of upstanding spaced lugs on said second side of said clutch plate, a diametrically opposed pair of said lugs being bifurcated, a pair of diametrically opposed pins being mounted in said hollow drive knob and extending radially inwardly thereof, said pins being located between said bifurcations of said pair of clutch plate lugs, whereby rotation of said drive knob will be imparted to said clutch plate by the cooperation of said pins and said bifurcations and said clutch plate and said drive knob can independently shift axially.

25. The structure claimed in claim 24 wherein said yieldable means comprises a plurality of springs, one end of each of said springs being located in a socket formed therefor in the interior of said hollow drive knob, the other end of each of said springs abutting said second side of said clutch plate.

* * * * *

UNITED STATES PATENT AND TRADEMARK OFFICE
CERTIFICATE OF CORRECTION

PATENT NO. : 4,442,964
DATED : April 17, 1984
INVENTOR(S) : Carl T. Becht

It is certified that error appears in the above–identified patent and that said Letters Patent are hereby corrected as shown below:

In Claim 1, col. 11, line 14, after "driver" insert--
actuator by said staple driver actuator shifting means only when the distance between said fixed jaw and said movable jaw falls within said working gap of said instrument.--

Signed and Sealed this

Fourth Day of December 1984

[SEAL]

Attest:

GERALD J. MOSSINGHOFF

Attesting Officer

Commissioner of Patents and Trademarks